United States Patent [19]

Marion

[11] Patent Number: 5,057,069

[45] Date of Patent: Oct. 15, 1991

[54] PROCESS AND DEVICE TO FOLD STRIPS OF SWABS

[76] Inventor: Louis Marion, Vieux bourg de Gondamine, 42230 Saint Victor sur Loire, France

[21] Appl. No.: 443,703

[22] Filed: Nov. 29, 1989

[30] Foreign Application Priority Data

Dec. 1, 1988 [FR] France ................. 88 16491

[51] Int. Cl.$^5$ ............... B31B 45/16; B31B 45/18; B31B 45/30
[52] U.S. Cl. .................... 493/395; 493/405; 493/426; 493/435; 493/445; 493/456; 493/463
[58] Field of Search ............ 493/395, 397, 405, 407, 493/426, 435, 444, 445, 456, 463

[56] References Cited

U.S. PATENT DOCUMENTS

| 1,501,774 | 7/1924 | Heeter et al. | 493/444 |
|---|---|---|---|
| 1,693,147 | 11/1928 | King | 493/444 |
| 1,980,532 | 11/1934 | Kahn | 493/444 |
| 2,954,974 | 10/1960 | Kellett | 493/444 |
| 3,901,501 | 8/1975 | Kistner | 493/444 |
| 4,083,552 | 4/1978 | Sioman | 493/444 |
| 4,487,598 | 12/1984 | McDonald | 493/463 |
| 4,569,672 | 2/1986 | Marion et al. | 493/444 |
| 4,601,695 | 7/1986 | Pazzi | 493/418 |
| 4,699,031 | 10/1987 | D'Angelo et al. | 493/463 |

FOREIGN PATENT DOCUMENTS 0056353 7/1982 European Pat. Off. .
2564812 11/1985 France .

Primary Examiner—William E. Terrell
Attorney, Agent, or Firm—Eckert Seamans Cherin & Mellott

[57] ABSTRACT

A method and apparatus for folding a length of material includes forming first and second transverse folds at opposite ends of the material whereby the material defines first and second end parts and a central part. Longitudinal corrugations are formed in the first and second end parts in order to reduce a transverse dimension of the first and second end parts. A third transverse fold is formed in the central part in order to bring the first and second end parts into superposition. In the resulting folded material, edges of the first and second end parts are recessed inward from edges of the central part.

8 Claims, 3 Drawing Sheets

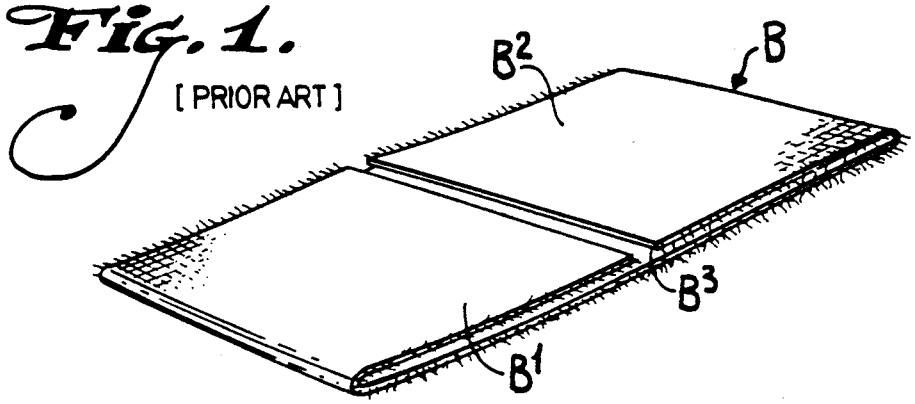

PROCESS AND DEVICE TO FOLD STRIPS OF SWABS

The invention concerns a process and device to fold strips of textile materials, swabs in particular.

The object of the invention relates to the technical sector of means for processing supple materials rolled up in strips or sheets and cut to length with a view to being packed.

Machines meant to continuously and automatically produce swabs from spools which are unrolled in order to bring the strips towards means to cut to length, then means to cross fold the strips and finally means to pack the folded strips, are known.

When the swabs are folded into four, as is the case with a machine covered by a French patent No. 8100687 the applicant of which is also the holder, the end parts (B1-B2) of the strip (B) which are successively folded onto the central part (B3) tend to separate transversally under the squashing effect of the cylinders for folding and fray, showing threads projecting from the width of the strip, as illustrated in FIGS. 1 and 2. It is understood that this phenomenon is harmful to the satisfactory finish of the product and subsequent packing, particularly when several swabs are packed in one bag or box.

These disadvantages are overcome when the process and device according to the invention which enable a swab to be folded into four in a clean manner, without projecting or fraying at the end parts, in a continuous manner in a machine between the distribution station and the packing station.

With this in mind and according to a first characteristic, the first and second folds of the end parts of the strip cut to length are simultaneously made with a reduction in width tranversally so that after the third fold of the central part of the swab and the superimposition of the two folds, edges of the said end parts are recessed inward from edges of the central part.

Another feature is found in the fact that the transversal reduction of the end parts of the strip cut to length is obtained by counter-parts made intergral of the first and second folding means and formed in order to force the said ends to partially penetrate into the circular grooves made on a drive cylinder and a backing roll between which the strip passes.

According to another characteristic, the counter-parts are made in the form of a comb fixed at the pinked part of the folding means and made up of alternate convex projections with recesses.

These characteristics and others will be made apparent in the description which follows.

In order to clarify the object of the invention, however, without limiting it, it is illustrated by the accompanying drawings:

FIGS. 1 and 2 illustrate a perspective view and a top view of a swab folded according to the prior art.

FIGS. 3, 4 and 5 are schematic views showing successive folds of the swab.

Figure 4:
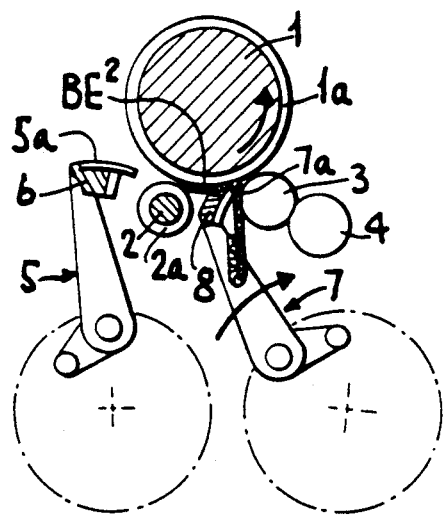

In order to have a fuller understanding of the object of the invention, it shall be described below in a non limiting form illustrated in the figures of the drawings.

The swabs to be folded into four are distributed from spools, cut to length and fed towards the folding means by well known components associated to one another on a main frame. The machine thus designed enables the strips required to produce swabs, to be cut, folded and packed automatically and continuously. As these devices are known, they have not been illustrated, the scope of the invention starts at the level of the first folding of the strip (BE) as shown in FIG. 3.

The strip positively driven by draw-off rolls upstream, vertically runs down through a channel provided with a combined blowing and suction system, runs between cutting cylinders standing by and arrives in front of first cylindrical roll (1) with multiple grooves (1a) into which retractable pallets (not represented) are housed which are provided to separate the strips cut upstream.

Second cylindrical roll (2) and third cylindrical roll (3) are applied under elastic pressure underneath the cylinder (1) whereas a fourth cylindrical roll (4) is also applied against the third roll (3). The second roll (2) is provided with multiple grooves (2a) of the same type as the grooves (1a) of the first roll (1), whereas rolls (3) and (4) are smooth. When the end part of (BE1) of the strip is against the second roll (2), a first folding means (5) is activated by any means to be applied by a first folding edge (5a) formed with teeth, against the said part (BE1) which is thus engaged and held between the second roll (2) and the first roll (1) with a view to forming the first fold.

Figure 6:
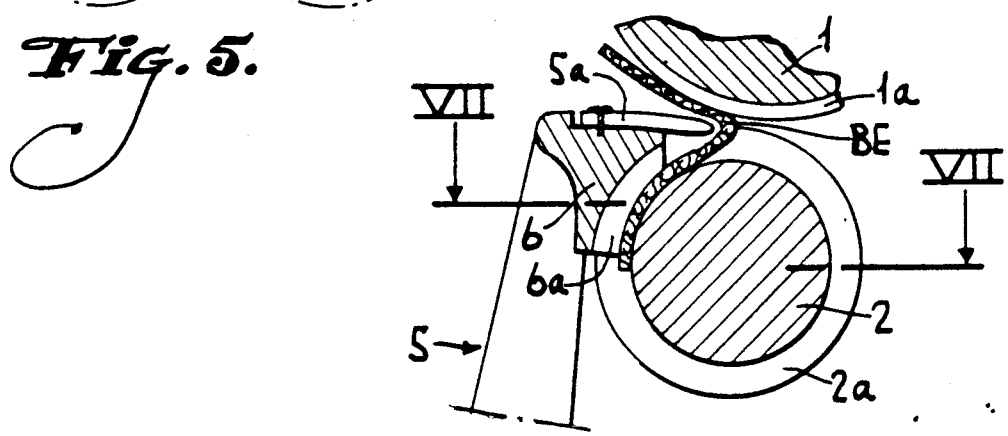
FIG. 6 is a sectional view on a larger scale illustrating the formation of the transversal reduction of the end parts of the swab.
Figure 7:
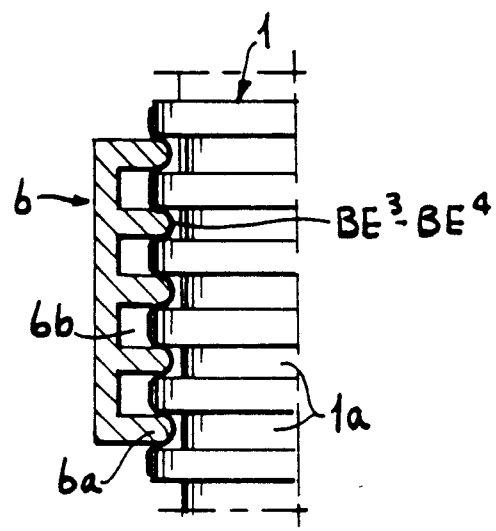
FIG. 7 is a top and sectional view taken on the line 7—7 of FIG. 6.

At this point, the cutting cylinders upstream are controlled to cut the strip to the desired length, then by rotating the first roll (1), the folded part of the strip runs between the first roll (1) and second roll (2), whereas the first folding means (5) reverses slightly then comes forward again so that a counter-part (6), made integral to the bottom side of the part (5a) and forming a comb by its alternate convex projections (6a) with recesses (6b), is pressed against the second roll (2) forcing the end part (BE1) of the strip to be penetrated in the grooves (2a) of the said second roll (FIGS. 3, 6 and 7). In this way, it is understood that this part of the strip, corrugated by the comb, has a reduced transverse dimension.

In the same way, when the rear end (BE2) of the strip is released by the first roll (1) and the second roll (2), a second folding means (7) is activated in order to form the second fold by a second folding edge (7a) urging the strip between the first roll (1) and the third roll (3) as shown in FIG. 4. As previously, the second folding means (7) has a counter-part (8) fixed above the second folding edge (7a) so that after a slight reverse movement and then forward movement, convex projections (7b) of the comb of the counter-part (8) form corrugations on the part (BE2) of the strip when it passes.

Figure 5:
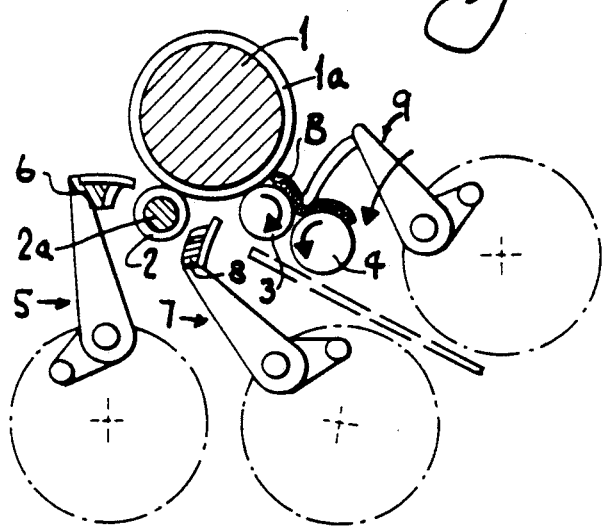

Therefore, the strip with its end (BE1) and (BE2) is above rolls (3) and (4) in order to form the third central fold, using a third conventional folding means (9) (FIG. 5), then the strip is discharged towards the packing station.

Figure 8:
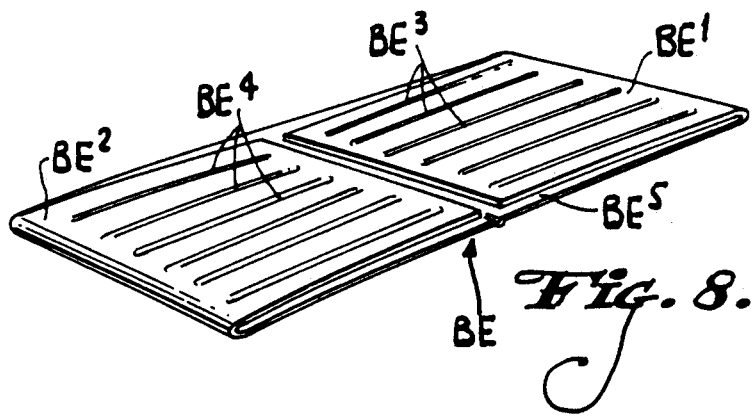
FIG. 8 is a perspective view showing a swab made according to the invention with its end parts folded back to the central part.
Figure 9:
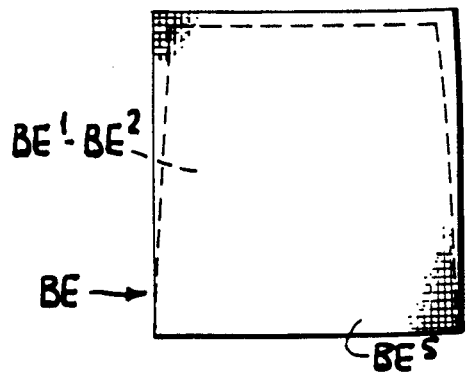
FIG. 9 is a top view illustrating the swab of FIG. 8 fully folded.

As clearly shown in FIGS. 8 and 9, the swab thus produced, has end parts (BE1) and (BE2) with corrugations (BE3) and (BE4) giving them a smaller width than the central part (BE5) which enables, once the third fold has been formed, a swab with clean and non-frayed edges to be obtained facilitating the subsequent packing and improving the finish.

I claim:

1. A method of folding a length of material, comprising the steps of:
   forming first and second transverse folds at opposite ends of the material whereby the material defines first and second end parts and a central part;
   forming longitudinal corrugations in the first and second end parts to reduce a transverse dimension of the first and second end parts; and,
   forming a third transverse fold in the central part, whereby the first and second end parts are brought into superposition and edges of the first and second end parts are recessed inward from edges of the central part.

2. The method according to claim 1, wherein the longitudinal corrugations are formed by urging the material of the second end part into a first plurality of grooves defined on a periphery of a first cylindrical roll, and by urging the material of the first end part into a second plurality of grooves defined on a periphery of a second cylindrical roll.

3. The method according to claim 2, wherein the urging is performed by a first comb defining a first plurality of projections, the first comb being moved such that each of the first plurality of projections descends into one of the second plurality of grooves, and a second comb defining a second plurality of projections, the second comb being moved such that each of the second plurality of projections descends into one of the first plurality of grooves.

4. The method according to claim 2, further comprising elastically biasing the second cylindrical roll toward the first cylindrical roll, and wherein the first transverse fold is formed by urging the material between the first and second cylindrical rolls.

5. The method according to claim 2, further comprising elastically biasing a third cylindrical roll toward the first cylindrical roll, and wherein the second transverse fold is formed by urging the material between the first and third cylindrical rolls.

6. The method according to claim 3, wherein a first folding edge is attached for movement with the first comb, the second cylindrical roll is elastically biased toward the first cylindrical roll, and movement of the first folding edge urges the material between the first and second cylindrical rolls.

7. The method according to claim 3, wherein a second folding edge is attached for movement with the second comb, a third cylindrical roll is elastically biased toward the first cylindrical roll, and movement of the second folding edge urges the material between the first and third cylindrical rolls.

8. A device for folding a length of material, comprising:
   a first cylindrical roll which is rotatable on a longitudinal axis and which defines a first plurality of grooves on its periphery,
   a second cylindrical roll which is rotatable on a longitudinal axis and which defines a second plurality of grooves on its periphery, the second cylindrical roll being parallel to and elastically biased toward the first cylindrical roll;
   a third cylindrical roll which is rotatable on a longitudinal axis, the third cylindrical roll being parallel to and elastically biased toward the first cylindrical roll;
   a fourth cylindrical roll which is rotatable on a longitudinal axis and elastically biased toward the third cylindrical roll;
   a first comb defining a first plurality of projections, the first comb being movable such that each of the first plurality of projections descends into one of the second plurality of grooves;
   a first folding edge attached for movement with the first comb, the first folding edge being insertable between the first and second cylindrical rolls;
   a second comb defining a second plurality of projections, the second comb being movable such that each of the second plurality of projections descends into one of the first plurality of grooves;
   a second folding edge attached for movement with the second comb, the second folding edge being insertable between the first and third cylindrical rolls; and,
   a third folding edge which is movable for insertion between the third and fourth cylindrical rolls.

* * * * *